(12) United States Patent
Dula-White

(10) Patent No.: US 11,638,662 B2
(45) Date of Patent: May 2, 2023

(54) SLEEVE TO AID IN WOUND TREATMENT

(71) Applicants: Lakia White, Rosedale, NY (US); Shamel White, Rosedale, NY (US)

(72) Inventor: Nina Dula-White, Brooklyn, NY (US)

( * ) Notice: Subject to any disclaimer, the term of this patent is extended or adjusted under 35 U.S.C. 154(b) by 389 days.

(21) Appl. No.: 15/998,849

(22) Filed: Aug. 17, 2018

(65) Prior Publication Data
US 2019/0053953 A1    Feb. 21, 2019

Related U.S. Application Data

(60) Provisional application No. 62/547,229, filed on Aug. 18, 2017.

(51) Int. Cl.
*A61F 13/06* (2006.01)
*A61F 13/10* (2006.01)
*A61F 13/00* (2006.01)

(52) U.S. Cl.
CPC .. *A61F 13/00063* (2013.01); *A61F 13/00042* (2013.01); *A61F 13/064* (2013.01); *A61F 13/10* (2013.01); *A61F 2013/00093* (2013.01); *A61F 2013/00217* (2013.01); *A61F 2013/00289* (2013.01)

(58) Field of Classification Search
CPC .......... A61F 13/00042; A61F 13/00063; A61F 13/064; A61F 13/10; A61F 2013/00289; A61F 2013/00217; A61F 2013/00093
See application file for complete search history.

(56) References Cited

U.S. PATENT DOCUMENTS

| | | | |
|---|---|---|---|
| D392,074 S * | 3/1998 | Witkin | A41D 13/065 D29/122 |
| 6,399,852 B1 * | 6/2002 | Barron | A61F 13/0269 602/41 |
| 6,932,785 B1 * | 8/2005 | Shesol | A61F 13/145 602/79 |
| 6,964,062 B1 * | 11/2005 | Chen | A41D 13/065 2/22 |
| 7,004,922 B1 * | 2/2006 | Shesol | A01K 13/006 119/856 |
| 8,733,296 B1 * | 5/2014 | Douglas | A01K 13/006 119/850 |
| 8,992,495 B1 * | 3/2015 | Howell | A01K 23/00 604/385.09 |
| D774,280 S | 12/2016 | Hakeem | |
| 2009/0062753 A1 * | 3/2009 | Ma | A61F 13/8405 604/290 |
| 2009/0112141 A1 * | 4/2009 | Derr | A61F 13/00063 602/53 |
| 2010/0024088 A1 | 2/2010 | Griefer | |
| 2012/0174875 A1 * | 7/2012 | Wetzel | A01K 21/00 119/838 |

(Continued)

*Primary Examiner* — Camtu T Nguyen
(74) *Attorney, Agent, or Firm* — Morrison & Foerster LLP

(57) ABSTRACT

The present disclosure is directed to a therapeutic sleeve for a medical patient. The sleeve has an interior side and an exterior side. The sleeve can include a fastener on the interior side. A wound care component such as an absorbent pad can be fastened to the interior side of the sleeve. The wound care component can be removed and replaced when it expires. The sleeve can be fabricated from stretch fabric, allowing the sleeve to conform to a patient's arm or leg.

8 Claims, 2 Drawing Sheets

(56) References Cited

U.S. PATENT DOCUMENTS

2013/0218105 A1* 8/2013 Blumenfeld ....... A41D 13/0543
            604/293
2014/0131402 A1  5/2014 Holmes
2017/0119068 A1* 5/2017 Beckenholdt ........ A41D 13/065

* cited by examiner

SLEEVE TO AID IN WOUND TREATMENT

CROSS-REFERENCE TO RELATED APPLICATION

This application claims the benefit of U.S. Provisional Application No. 62/547,229, filed Aug. 18, 2017, the entire contents of which is incorporated herein by reference.

FIELD OF THE DISCLOSURE

This disclosure relates to sleeves and applications for said sleeves. More particularly, this disclosure relates to reusable sleeves that can be used to aid in the treatment of wounds.

BACKGROUND

Some health care procedures, such as dialysis and cancer treatment, require frequent medical care. Often, this recurring medical care may be administered through an access site on a patient's body. Patients must diligently keep the access site clean and protected to both minimize opportunity for infection and allow for efficient treatment sessions. Many patients use ointments to help numb the access site or to help keep the access site clean. Additionally, because treatments via access sites inherently penetrate the skin, many patients can experience residual bleeding after treatment is completed.

SUMMARY

Currently, there is no easy solution to deal with ointments or residual bleeding that also frees a patient's hands to complete tasks other than tending to the wound. Applicant has developed a sleeve that may be used to both protect a patient's wound or access site from the environment and tend to the wound or access site while freeing a patient's hands for other activities. Specifically, Applicant has created a sleeve that can apply a wound care component, such as gauze, to the access site to hold ointment in place, absorb any residual blood, and/or provide cushioning to the wound.

The present disclosure provides a therapeutic sleeve comprising an interior side comprising a first fastening component, an exterior side, at least one opening, and a wound care component comprising a second fastening component, wherein the second fastening component removably attaches to the first fastening component. The second fastening component may be on a first side of the wound care component and a medication may be on a second side of the wound care component opposite the first side. The medication may be a numbing ointment. The wound care component may comprise gauze. The wound care component may be disposable. The first fastening component and the second fastening component may comprise Velcro.

The therapeutic sleeve may comprise a second opening opposite the first opening, wherein the second opening has a diameter smaller than the diameter of the first opening. Alternatively, the first opening and the second opening may have substantially the same diameter. The therapeutic sleeve may comprise spandex. The therapeutic sleeve may have a length of at least 9 inches.

In a second aspect, the present disclosure provides a method of applying a therapeutic sleeve to a patient's arm comprising applying ointment to a first side of a wound care component, wherein a second side of the wound care component comprises a second fastening component, fastening the second fastening component to a first fastening component, the first fastening component attached to an interior of the therapeutic sleeve, and sliding the therapeutic sleeve along a patient's arm until the wound care component is positioned against a wound of the patient's arm. The ointment may be a numbing ointment. The wound care component may comprise gauze. The wound care component may be disposable.

The first fastening component and the second fastening component may comprise Velcro. The second fastening component may be removably attached to the first fastening component.

The therapeutic sleeve may comprise spandex. The therapeutic sleeve may comprise a first opening and a second opening. The second opening may have a diameter smaller than a diameter of the first opening. Alternatively, the first opening and the second opening may have substantially the same diameter.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Additional advantages will be readily apparent to those skilled in the art from the following detailed description. The examples and descriptions herein are to be regarded as illustrative in nature and not restrictive.

BRIEF DESCRIPTION OF THE DRAWINGS

Exemplary embodiments are described with reference to the accompanying figures, in which.

DETAILED DESCRIPTION

Figure 1:
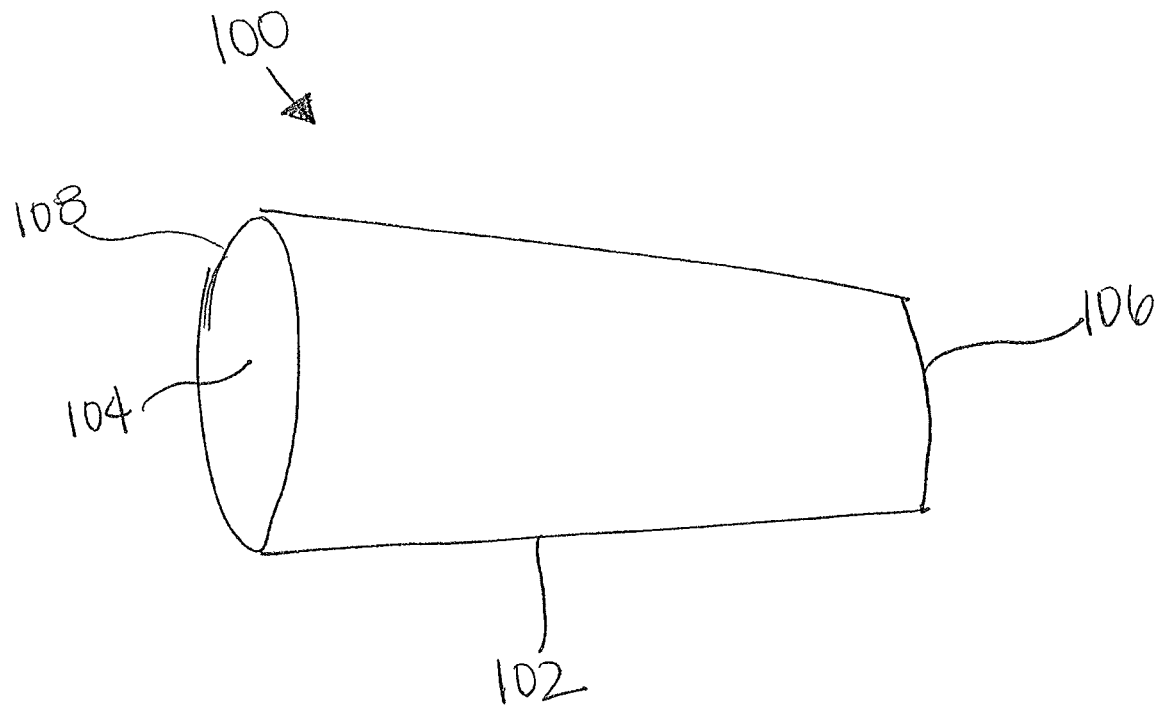
FIG. 1 provides a three-dimensional depiction of a sleeve according to some embodiments disclosed herein.

Applicant has developed a product to ease the effects of some types of health care treatments. Specifically, certain types of health care treatment require repeated access to a patient's body to administer therapeutic compounds. As a result, patients must keep these treatment sites, or access sites, clean and protected. Accordingly, Applicant has created a sleeve that may help protect a wound from the outer environment and may help hold a wound care component at the wound.

For sleeves that help a patient treat and hold a wound care component to the wound or access site, a removable wound care component may be fastened to the interior of the sleeve. For example, the wound care component may be in the form of a bandage or absorbent pad such as gauze or gauze pads. A wound care component may be used to absorb any residual blood or collect any excess ointment from the wound or access site. In addition, a wound care component may serve as cushioning to the wound. A wound care component can be removable from the sleeve. For example, a wound care component may be removed from a sleeve and replaced with a clean wound care component or a different type of wound care component.

In some embodiments, a wound care component may be disposable. For example, a soiled wound care component may be removed from a sleeve and replaced with a clean wound care component. In other embodiments, a wound care component can be reusable. For example, a soiled wound care component may be removed from a sleeve. Reusable wound care components may be washed or otherwise cleaned after being removed from the sleeve. In addition, a reusable wound care component may be re-fastened on an interior of a sleeve.

A sleeve according to some embodiments described herein may be applied to various regions of a patient's body. For example, a sleeve may be applied to an arm, leg, finger, toe, torso, or any other body part including the upper, lower, or both parts of the body part. In embodiments where a sleeve is applied to a patient's arm or leg, a conical frustum-shaped sleeve may allow for a skintight fit along the full length of the sleeve. In other embodiments, a sleeve may be in the shape of a cylinder. Some embodiments may have one or more seams running the length or width of the sleeve. Other embodiments may be seamless.

A sleeve according to some embodiments described herein may be fabricated from various different materials. For example, a sleeve may be fabricated using cotton, leather, polyester, rayon, knit materials, any combination thereof, and/or the like. For example, a sleeve may be fabricated using synthetic materials including stretch materials such as spandex. Additionally, other materials can be used to fabricate the sleeve such as thread, buttons, zippers, hook-and-eye closures, elastic, snaps, pins, Velcro, buckles, glue, or any combination thereof, and/or the like. In some embodiments, the sleeve can be made from washable and reusable material.

A sleeve according to embodiments described herein may vary in size depending on the size of the patient and the specific region of the body intended to benefit from a sleeve. For instance, a sleeve for a child patient may be smaller than a sleeve for an adult patient. Similarly, a sleeve for a forearm of an arm may be smaller than a sleeve for a thigh of a leg. Accordingly, sleeves described herein may be a variety of sizes. A circumference of a sleeve opening may be between five inches and twenty-five inches. A length of a sleeve may be between six inches and twenty-four inches. In some embodiments, a length of a sleeve may be a minimum of nine inches.

Some embodiments disclosed herein may utilize a removable wound care component. In some embodiments, the wound care component may be gauze. In other embodiments, the wound care component may include cotton, linen, synthetic material, a bandage, absorbent material, any combinations thereof, and/or the like. In some embodiments, removable wound care components may be used to absorb residual blood or other bodily fluids. A wound care component may be used to absorb excess medication such as a numbing agent. In some embodiments, a wound care component may hold in place medication such as ointment to a wound or an access site. For example, ointment may be applied to a clean wound care component. The wound care component with ointment applied may be attached to a sleeve. In another embodiment, a wound care component may act as a barrier between a wound or an access site and a sleeve such as a cushioning barrier. The wound care component may be removed from a sleeve at any time. For example, the wound care component may be removed once the wound care component becomes saturated or soiled. Clean wound care components may be fastened to a sleeve approximately where a saturated or soiled wound care component was removed.

A removable wound care component may be a variety of sizes. In some embodiments, wound care components may be of any commercially available wound treatment dressings. For example, a wound care component may be a cotton pad or a gauze pad. Cotton pads or gauze pads may be of any commercially available size, such as 2"×2", 2"×3", 3"×3", 4"×4", or any other available size. Wound care components may also be modified according to a patient's wound or access site. For example, a commercially available gauze pad may be cut or folded to suit a patient's needs.

Some embodiments of a sleeve may include a fastener. For example, a fastener may enable a wound care component to be temporarily fastened to an interior of the sleeve. A fastener may include any variation of reusable adhesive such as snaps, Velcro, reusable adhesive film, magnets, hooks, any combinations thereof, and/or the like. In some embodiments, a fastener may be Velcro. For example, one side of a piece of Velcro may be attached to an interior of a sleeve, and a second side of a piece of Velcro may be attached to a side of the wound care component. In some embodiments, one side of a piece of Velcro may be attached to an interior of a sleeve. A second side of a piece of Velcro may be attached to a side of a wound care component. A Velcro fastener may be attached to a sleeve or wound care component with thread, glue, or other fastening means. An opposing side of a wound care component may be facing a wound or an access site when a sleeve is applied to a patient.

In some embodiments, a fastener may include two or more components. For example, one component of a fastener material may be attached to a wound care component, and a complementary component of a fastener material may be attached to a sleeve interior. Joints between a fastener and a wound care component and between a fastener and a sleeve may be temporary and removable or permanent and irreversible.

FIG. 1 depicts an example sleeve 100 according to some embodiments. A sleeve 100 can be conical frustum-shaped as shown. The sleeve may have an opening 106 of a sleeve which may be smaller than an opposing opening 104. A conical frustum-shaped sleeve 100 may allow a sleeve to conform to a patient's body part along a length 102. In many situations, a patient's arm or leg will vary in girth along a length of the arm or leg. Accordingly, one opening 106 of a sleeve 100 may be smaller than an opposing opening 104 of a sleeve 100, which may allow a sleeve 100 to conform to a patient's arm or leg along a length 102 of a sleeve 100.

Sleeves according to other embodiments may be cylindrically-shaped. A cylindrically-shaped sleeve may have openings substantially similar in size. For example, opening 104 may be substantially similar in size to opening 106.

In some embodiments, the sleeve described herein may have a single opening. For example, opening 104 may be the only opening of a sleeve 100. In some embodiments where a sleeve 100 is applied to an arm, opposing end 106 may be fashioned to conform to a hand, much like a glove. In some embodiments where a sleeve 100 is applied to a leg, opposing end 106 may be fashioned to conform to a foot, much like a sock.

A sleeve according to some embodiments described herein may have one or more seams along a length 102 of a sleeve 100. For example, two or more edges of a sleeve material may be joined to form a conical frustum or cylindrical shaped (or any other shape) sleeve according to embodiments described herein. Two or more edges of a sleeve may be joined by thread, glue, staple, snaps, hooks, zippers, any combinations thereof, and/or the like.

A sleeve according to some embodiments may have one or more seams along a circumference 108 of a sleeve 100. For example, two or more edges of a sleeve material may be joined to form a conical frustum or cylindrical shape, or any other shape according to embodiments described herein.

A sleeve may be fabricated using various methods. Two or more edges of a sleeve may be joined by thread, buttons, zippers, hook-and-eye closures, elastic, snaps, pins, Velcro, buckles, glue, any combination thereof, and/or the like. Any method of fabrication may be carried out manually or by machine. For example, a sleeve may be hand-sewn or machine-sewn.

Sleeves according to embodiments described herein may be applied to various regions of a patient's body. For example, a sleeve may be applied to a patient's arm or a patient's leg. In some embodiments, a sleeve may be slid onto a patient's arm or leg to a desired position. In other embodiments, a sleeve may be wrapped around a patient's arm or leg. A sleeve may be held in place on a patient's arm or leg using thread, glue, staple, zipper, any combinations thereof, and/or the like.

Figure 2:
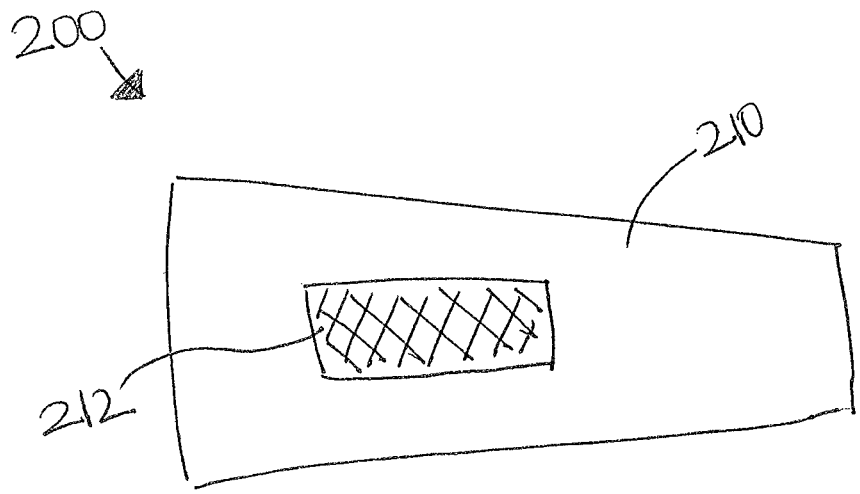
FIG. 2 provides a two-dimensional depiction of an interior of a sleeve according to some embodiments.

FIG. 2 is a depiction of a sleeve interior 200 according to some embodiments described herein. Material 210 of a sleeve may include of cotton, leather, polyester, rayon, knit materials, spandex, any combination thereof, and/or the like.

Fastener 212 may adhere a wound care component (not shown) to a sleeve interior 200. Fastener 212 may be located at any position along a length of a sleeve 200. Fastener 212 may be located at any position along a width of a sleeve 200. Fastener 212 may include of any variation of reusable adhesive such as snaps, Velcro, reusable adhesive film, magnets, any combinations thereof, and/or the like.

In some embodiments, fastener 212 may include multiple components. For example, fastener 212 may include Velcro, which includes two complementary components. In such embodiments, one component of a two-component fastener may be attached to sleeve interior 200. A second component of a two-component fastener may be attached to a wound care component (not shown).

When applying a sleeve to a patient, the wound care component may be attached to a sleeve interior using fastener 212. For example, ointment may be applied to a clean wound care component. A wound care component containing ointment may be attached to fastener 212. A sleeve may be applied to a patient's body. The sleeve may be positioned along a patient's body according to a location of a patient's wound or access site.

Figure 3:
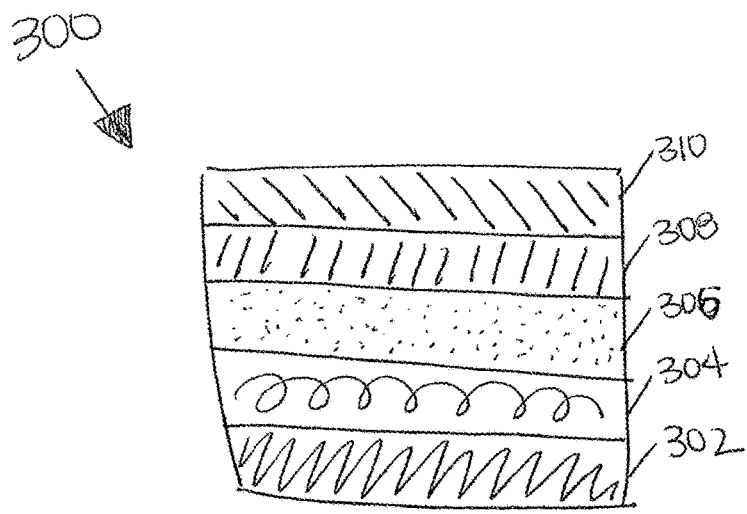
FIG. 3 illustrates example possible layers of material of a sleeve according to some embodiments.

FIG. 3 is an example layer configuration 300 of materials according to some embodiments disclosed herein. In embodiments depicted in FIG. 3, a sleeve may include two sleeve material layers, 302 (exterior) and 304 (interior), excluding optional fasteners and wound care components. Exterior layer 302 and interior layer 304 may include cotton, leather, polyester, rayon, knit materials, or any combination thereof, and/or the like. Layers 302 and 304 may include identical materials or different materials. Layers 302 and 304 may include a single piece of material joined to form a double-layered sleeve. Layers 302 and 304 may include multiple, distinct pieces of material.

A sleeve according to other embodiments may include a single layer of material. In such embodiments, a single layer of sleeve material may be cut to a desired size. Sleeve material may be shaped and finished, employing one or more fabrication methods including thread, glue, staple, any combinations thereof, and/or the like. Opening edges of a sleeve including a single layer of material may be hemmed or otherwise finished. Hemming or otherwise finishing edges may prevent runs in the material or an undesirable aesthetic.

In some embodiments, exterior layer 302 may include multiple layers of material. In some embodiments, interior layer 304 may include multiple layers of material. Multiple layers of sleeve material may be used to increase durability, thickness, and even absorbency.

An optional fastener may include layers 306 and 308. In some embodiments, a fastener may include any variation of reusable adhesive such as snaps, Velcro, reusable adhesive film, magnets, any combinations thereof, and/or the like. For example, a fastener may include Velcro. A fastener such as Velcro may include layers 306 and 308, where layer 306 and layer 308 may include complementary components of Velcro that adhere together. In other embodiments, a fastener such as a snap fastener may include layer 306 and layer 308, where layer 306 and layer 308 each include a male or female component of a snap fastener.

In some embodiments, an optional fastener may include a single layer. For example, a fastener may include double-sided adhesive tape or a single layer of glue.

Wound care component 310 may be an innermost layer of layer configuration 300 according to some embodiments. A wound care component may include cotton, linen, synthetic material, a bandage, absorbent material, any combinations thereof, and/or the like. Wound care component 310 may be temporarily or permanently adhered to a fastener layer. For example, a wound care component may be adhered to a complementary component of a two-component fastener, such as Velcro or a snap fastener.

In some embodiments, wound care component 310 may include multiple layers. For example, some patients may use ointment to numb or clean an access site. Thus, wound care component 310 may include, for example, an absorbent pad layer and an ointment layer. A sleeve according to embodiments described herein may hold wound care component 310 to a patient's wound or access site.

In some embodiments, wound care component 310 may be disposable. In some embodiments, wound care component 310 may include a gauze pad. For example, wound care component 310 may be unfastened from sleeve interior. A clean gauze pad may be fastened to a sleeve interior according to embodiments described herein.

Wound care component 310 may be reusable in some embodiments. For example, wound care component 310 may be unfastened from sleeve interior when the wound care component expires or becomes soiled. In some embodiments, a wound care component may be washed, sanitized, and re-fastened to a sleeve interior.

Figure 4:
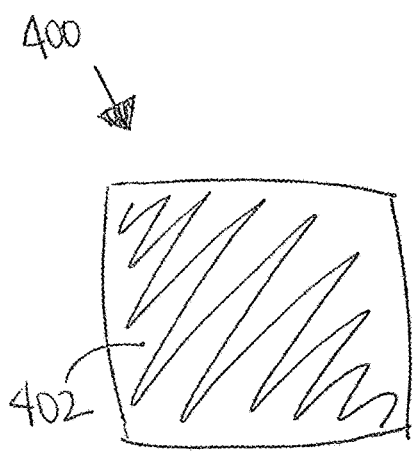
FIG. 4 illustrates a first example side of an optional wound care component according to some embodiments.

FIG. 4 illustrates an example side of wound care component 400 according to some embodiments described herein. In some embodiment, wound care component material 402 may face a wound or an access site when wound care component 400 is fastened to a sleeve interior and a sleeve is applied to a patient. In some embodiments, wound care component material 402 may be absorbent. In some embodiments, wound care component material 402 may serve as cushioning. In some embodiments, medical care treatment such as ointment may be applied to wound care component material 402. For example, ointment may be applied to wound care component material 402 such that when wound care component 400 is fastened to a sleeve and said sleeve is applied to a patient, the ointment is held in place against a patient's wound or access site.

Wound care component material 402 may include cotton, linen, synthetic material, a bandage, any combinations thereof, and/or the like.

Figure 5:
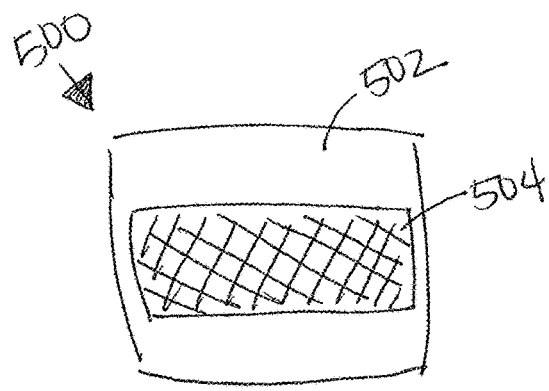
FIG. 5 illustrates a second example side of an optional wound care component according to some embodiments.

FIG. 5 illustrates an example opposing side 500 (to that depicted in FIG. 4) according to some embodiments described herein. In some embodiments, wound care component material 502 may include the same material as wound care component material 402. In some embodiments, wound care component material 502 may include a different material from wound care component material 402. In some embodiments, wound care component material 502 and wound care material 402 may include the same material, but wound care material 502 and wound care component material 402 may be subjected to different surface treatments. Wound care component material 502 may include cotton, linen, synthetic material, a bandage, absorbent material, any combinations thereof, and/or the like.

Fastener 504 may be attached to wound care component side 500. In some embodiments, wound care component side 500 may be fastened to an interior of a sleeve such that wound care component side 500 is facing a sleeve interior. Fastener 504 may be reusable, such that fastener 504 may be repeatedly fastened and un-fastened to a sleeve interior. In some embodiments, fastener 504 may include one component of a two-component fastener mechanism. For example, fastener 504 may be one component of Velcro or a snap fastener. Velcro and snap fasteners typically include two complementary components that link together.

Fastener 504 may be attached to wound care component material 502 using various methods. For example, fastener 504 may be sewn to wound care component material 502. Sewing may be by hand or by machine. In some embodiments, fastener 504 may be glued to wound care component material 502. Other embodiments may employ other adhesion methods to attach fastener 504 to wound care component material 502.

Fastener 504 may be attached to wound care component material 502 in various positions. In some embodiments, fastener 504 may be centered length-wise on wound care component material 502. In some embodiments, fastener 504 may be centered width-wise on wound care component material 502. In some embodiments, fastener 504 may be positioned off-center. For example, fastener 504 may be positioned closer to an edge of wound care component material 502 to minimize any negative interaction with elbow motion or knee motion. A position of fastener 504 may be dependent upon a patient's wound or access site location. In some embodiments, a position of fastener 504 may depend upon a region of a patient's body a sleeve is intended to be applied.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein. Finally, the entire disclosure of the patents and publications referred in this application are hereby incorporated herein by reference.

The invention claimed is:

1. A therapeutic sleeve comprising:
an interior layer having a first side and a second side;
an exterior layer on the first side of the interior layer, wherein the exterior layer excludes a fastener between the interior layer and the exterior layer;
a first fastening component on the second side of the interior layer;
a first opening and a second opening opposite the first opening; and
a wound care component comprising a second fastening component, wherein the second fastening component removably attaches to the first fastening component, and
wherein a diameter of the second opening is smaller than a diameter of the first opening such that the therapeutic sleeve forms a conical frustum-shape and is configured to surround an arm or leg of a patient such that the interior layer contacts the patient's arm or leg around the entire arm's or leg's circumference.

2. The sleeve of claim 1, wherein the second fastening component is on a first side of the wound care component and a medication is on a second side of the wound care component opposite the first side.

3. The sleeve of claim 2, wherein the medication is a numbing ointment.

4. The sleeve of claim 1, wherein the wound care component comprises gauze.

5. The sleeve of claim 1, wherein at least one of the first fastening component and the second fastening component comprises hooks.

6. The sleeve of claim 1, wherein the interior layer and the exterior layer comprise synthetic material.

7. The sleeve of claim 1, wherein the wound care component is disposable.

8. The sleeve of claim 1, wherein the therapeutic sleeve has a length of at least 9 inches.

* * * * *